United States Patent [19]

Taigen

[11] Patent Number: 4,964,401
[45] Date of Patent: Oct. 23, 1990

[54] WEIGHTLIFTING BELT

[76] Inventor: Roger L. Taigen, 3609 Ranch Rd. East, Altus, Okla. 73521

[21] Appl. No.: 414,467

[22] Filed: Sep. 29, 1989

[51] Int. Cl.$^5$ .......................... A61F 5/02; A61F 5/37; A63B 21/072; A63B 21/00
[52] U.S. Cl. ..................................... 128/78; 128/876; 272/123; 272/143; 2/338
[58] Field of Search ...................... 128/876, 78; 2/338, 2/339, 312; 272/123, 143; 273/DIG. 11, 30, 189 A

[56] References Cited

U.S. PATENT DOCUMENTS

| | | | |
|---|---|---|---|
| 1,275,522 | 8/1918 | Boylan | 273/143 |
| 2,084,305 | 6/1937 | Bach | 128/876 |
| 3,108,292 | 10/1963 | Bodnar | 128/876 |
| 3,659,843 | 5/1972 | Kojigian, Jr. | 272/143 |
| 3,888,245 | 6/1975 | Berntson | 273/143 |
| 4,132,229 | 1/1979 | Morrison | 128/876 |
| 4,239,211 | 12/1980 | Wilkerson | 273/143 |
| 4,396,013 | 8/1983 | Hasslinger | 128/876 |
| 4,685,668 | 8/1987 | Newlin, Jr. | 272/123 |
| 4,745,911 | 5/1988 | Bender | 273/123 |
| 4,799,675 | 1/1989 | Helmer | 273/123 |
| 4,802,667 | 2/1989 | Altner | 273/123 |

Primary Examiner—Robert A. Hafer
Assistant Examiner—Michael Brown
Attorney, Agent, or Firm—Laney, Dougherty, Hessin & Beavers

[57] ABSTRACT

A weightlifting belt including an elongated belt body adapted to encircle the abdominal region. A heavy duty webbing backup element extends over a major portion of the length of the belt body, and a lumbar support pad is secured to the center of the belt body. Strips of self-gripping fastener material are secured to opposite sides of the belt body adjacent its opposite ends, and form a first closure subassembly of a double closure system. A holding strap is secured to, and projects from, one end of the belt body, and is extendable through a buckle spaced along the belt body from the opposite end thereof. The holding strap carries self-gripping material positioned to engage an additional strip of such material carried between the ends of the belt body. This provides the second closure subassembly of the double closure system.

10 Claims, 1 Drawing Sheet

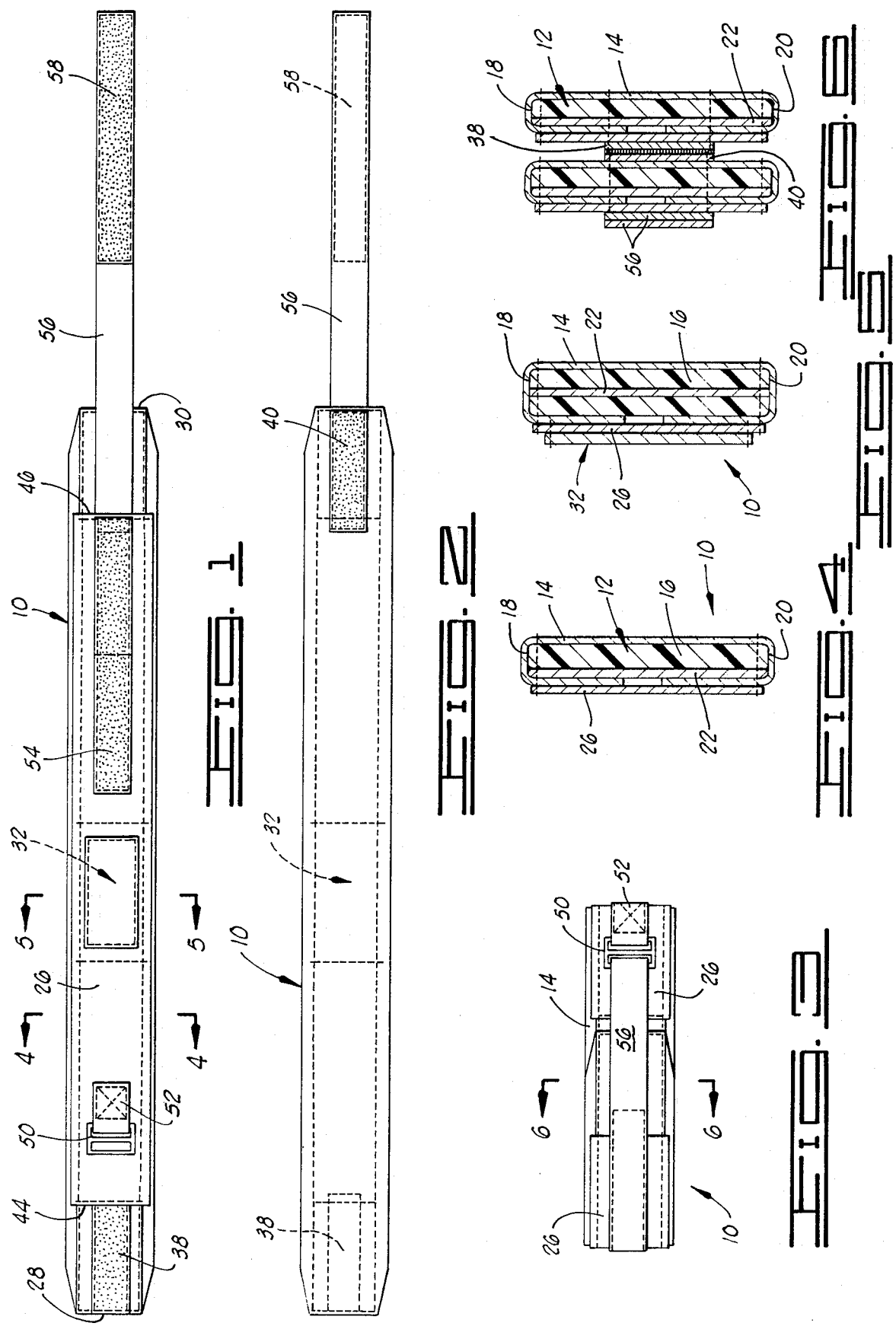

WEIGHTLIFTING BELT

FIELD OF THE INVENTION

This invention relates to a weightlifting belt used by body building and weightlifting practitioners for affording support to the lower torso and abdominal region during lifting of weights so as to prevent damage to the kidneys and internal organs, and injury to the lower spinal region.

BRIEF DESCRIPTION OF THE PRIOR ART

The current sport of power lifting involving the lifting of heavy weights has embued practitioners of that sport with an understanding that some danger to the muscles, organs and lower spinal region can occur unless the lower torso, including the abdominal area, is confined and supported by a belt during the lifting of the weights. Strain and internal pressure markedly increase with the lifting of very heavy weights, constituting a threat of serious injury unless adequate precautions are taken by the weightlifter.

Weightlifting belts are, in general, of from about three to about seven inches in width, with the most widely used width being about four inches. It is important that the belt be constructed so that it does not cut the flesh along its edges, that it does not curl, and that it not be able to undergo significant stretching during use.

One material which has heretofore been used in the construction of weightlifting belts is leather. Other materials which have been used include heavy duty nylon webbing, and a combination of superimposed materials made up in a laminated structure.

A belt in which the basic structural element is constructed of heavy duty nylon webbing is that which is depicted and described in U.S. Pat. No. 4,685,668. In this patent, a belt body made of heavy duty nylon webbing is provided, and the body includes backing strips secured to the webbing and a holding strap which is of sufficient length to permit it to be extended through a buckle, then doubled back and used for securing the belt in place around the body of the weightlifter.

BRIEF DESCRIPTION OF THE PRESENT INVENTION

The present invention is an improved weightlifting belt which is soft and comfortable to wear, affords excellent support for the torso and abdominal zone of the body during weightlifting exercises, and is lightweight and completely washable. The belt provides a unique double closure system which can be made to fit exactly the abdominal area of the particular user.

Broadly described, the weightlifting belt of the invention includes an elongated belt body which incorporates a soft, foam rubber pad which faces the body of the user and provides a comfortable, yet firm, support. The foam rubber pad is backed by a flat plate or strap of a fiber-plastic board of relatively high strength and good rigidity. The core, made up of the fiber-plastic plastic plate or strip and the foam rubber pad, is encased within an outer shell or sleeve which is made of a special CORDURA/SUPPLEX nylon material manufactured by the E. I. DuPont DeNemours Company of Wilmington, Del. The CORDURA/SUPPLEX nylon material is a soft lightweight material of high strength with a feel similar to cotton.

Secured to the side away from the body of the wearer of the outer shell or sleeve is a backup strap or element which is of substantially the same width as the core of the belt body. The backup element is a heavy duty webbing strapping material which extends over a major portion of the length of the belt body.

A lumbar support pad is carried at the central portion of the belt body and on the inner side thereof at a location to fit into the hollow at the base of the spine of the wearer, and thus provide lumbar support at this location. Short strips of mutually interengaging self-gripping fastener material are secured to the opposite sides of the belt body at locations adjacent its opposite ends. When the belt is wrapped around the torso of the user and fitted snugly to the user's body, a closure can be effected between the strips of fastener material to form a first closure subassembly in the unique double closure system of the present invention. An elongated flexible holding strap is secured to, and projects from, one end of the belt body. The holding strap is extendable through a buckle spaced along the belt body from the opposite end of the belt body from that from which the holding strap extends. The free end of the holding strap (extended through the buckle) carries self-gripping material which is positioned to engage an additional strip of such material carried between the ends of the belt body. This arrangement thus provides for the second closure subassembly of the double closure system. Thus, the self-gripping fastener material carried on the free end of the holding strap, when passed through the buckle and doubled back can then be pressed against the second strip of self-gripping fastener material to form the second closure subassembly.

The weightlifting belt, constructed in the manner described, is completely washable, and repeated washings do not deleteriously effect the strength of the weightlifting belt.

Another important object achieved by the described weightlifting belt is the provision of a high strength belt which affords good body support over a wide zone around the torso or abdominal region.

A further object of the invention is to provide a lower lumbar support pad as a part of the weightlifting belt of the invention, which pad is positioned to bear against the lower part of the spine when the belt is in proper position for weightlifting.

Another important object of the invention is to provide a weightlifting belt which can be secured snugly around the body of the weightlifter at the proper location by the use of a unique double closure system which assures that a proper fit affording full support will not be lost due to high opening forces being exerted against the belt tending to open it at a time when support is the most critical during the weightlifting exercise.

Additional objects and advantages of the invention, and features which are unique to the weightlifting belt of the invention, will be better understood as the following detailed description of a preferred embodiment of the invention is read in conjunction with the accompanying drawings which illustrate such preferred embodiment of the invention.

GENERAL DESCRIPTION OF THE DRAWINGS

FIG. 1 is a side elevation view of the weightlifting belt of the invention as it appears when the belt is viewed from the outer side thereof.

FIG. 2 is a side elevation view of the weightlifting belt of the invention as it appears when the belt is viewed from the inner side of the belt which faces, and bears against, the body of the wearer as the belt is used.

FIG. 3 is a detail view showing, in elevation, the overlapped end portions of the weightlifting belt after the double closure system of the invention (utilizing a first and second closure subassembly) has been employed to secure the belt in its supporting position.

FIG. 4 is a sectional view taken along line 4—4 of FIG. 1.

FIG. 5 is a sectional view taken along line 5—5 of FIG. 1.

FIG. 6 is a sectional view taken along line 6—6 of FIG. 3.

DETAILED DESCRIPTION OF A PREFERRED EMBODIMENT OF THE INVENTION

The primary structural element of the weightlifting belt of the invention is a belt body designated generally by reference numeral 10. The belt body 10 has a body side which faces the wearer of the belt and an outer side. The belt body 10 includes a core denominated generally by reference numeral 12, with the core encased in an outer shell or sleeve 14. The core 12 of the belt body 10 includes an elongated foam rubber pad 16 which has an upper edge 18 and a lower edge 20. The pad 1B is preferably made of foam rubber and is positioned to face the body of the wearer of the belt. Lending rigidity and support to the belt body 10 is a flat plate, strip or strap 22 of a plastic material having fibers embedded therein. The flat plate 22 is of rigid construction, and it is of relatively high strength. The width of the plate 22 is substantially equivalent to that of the resilient pad 16, and the plate bears flatly against the outer side of the pad as shown in FIG. 4 of the drawings.

The core 12, made up of the pad 16 and the plate 22, is surrounded by an outer shell or sleeve 14 which is preferably constructed of a relatively non-stretchable nylon fabric material. One such material is sold under the name CORDURA/SUPPLEX (trademarks of the E. I. DuPont DeNemours Company of Wilmington, Del.). The nylon fabric of which the outer shell or sleeve 14 is constructed is a high strength material having the feel of cotton, and is relatively lightweight. As shown in FIG. 4, the shell or sleeve 14 extends nearly completely around the core 12, and in some embodiments of the invention does, in fact, extend completely around and encase the core. The shell or sleeve 14 may also be described as having a body side 14a which faces the body of the wearer and an outer side 14b.

Secured to the outer side of the belt body 10 is a backup element or strap 26. The backup strap 26 has a width which is substantially the same as the width of the belt body 10. As shown in FIG. 1, the length of the backup strap 26 is less than the length of the elongated belt body, so that the backup strap terminates short of each of the ends of the belt body. In a preferred embodiment of the invention, the backup strap 26 terminates about four inches short of the respective opposite ends 28 and 30 of the belt body. The backup strap 26 is constructed of heavy duty webbing material, such as cargo webbing made of nylon.

In substantially the center of the belt body 10, and on the inner side thereof at a location to fit in the concavity of the lower spine, is a lower lumbar support pad designated generally by reference numeral 32. The lumbar support pad 32 is of generally rectangular configuration, and is from about three inches to about five inches in width as measured lengthwise of the belt, and from about three inches to about six inches in transverse width.

In order to provide a first closure subassembly forming a part of the double closure system of the weightlifting belt of the invention, a first strip of self-gripping fastener material 38 is secured to the outer side of the belt in the center of the belt, and adjacent the end 28 of the belt body. The self-gripping material can typically be the hook portion or the eye portion of a Velcro fastener combination. For the purpose of cooperating with, and engaging, the first strip 38 of self-gripping fastener material, a second strip 40 of such self-gripping fastener material is provided at the opposite end 30 of the belt body 10, and is located on the inner side of the belt. Stated differently, the second strip 40 is located on the opposite side of the belt body 10 from that side which carries the first strip 38 of self-gripping fastener material.

From the description of the locations of the first and second strips 38 and 40 of self-gripping fastener material, it will be perceived that when the belt is extended around the body with that side of the belt shown in FIG. 2 being adjacent the body, the fastener strip 40 of self-gripping material will pass over, and be engageable with, the outwardly facing side of the first strip 3B of such self-gripping material. This overlap engagement is shown in FIG. 6. In this way, the first closure subassembly constituting the first interlock of the double closure system of the invention is effected.

For purposes of further description, the backup strap 26 will be described as characterized by a pair of opposite ends 44 and 46 which extend transversely across the longitudinal axis of the belt body 10. As previously indicated, the ends 44 and 46 are each located about four inches from the respectively adjacent ends 28 and 30 of the belt body 10.

Spaced along the backup strap 26 about four inches from the end 44 thereof is a buckle 50 which is secured to the outer surface of the backup strap 26 by a fabric loop 52. Near the opposite end 46 of the backup strap 26, a third strip 54 of the self-gripping fastener material is secured along the longitudinal center line of the belt body 10, and extends from the end 46 of the backup strap to a location relatively near to the lumbar support pad 32. The self-gripping fastener material in the strip 54 can typically be either the loop or hook portion of Velcro material, and functions in a manner well understood in the art for cooperative engagement with another strip of this type (hereinafter described) carrying either the hooks or the loops as may be required for such engagement.

The weightlifting belt further includes an elongated holding strap 56. The holding strap 56 has a first end portion which is projected under the backup strap 26 for a short distance, and is sewn, or otherwise suitably secured, to the belt body 10. The holding strap 56 is preferably substantially narrower than the belt body and is elongated to provide a portion which extends beyond the end 30 of the belt body. This portion of the holding strap 56 is sufficiently narrow to pass through the opening provided in the buckle 50.

The holding strap 56 has secured to the outer side thereof (on the same side of the holding strap as the strip 54 of self-gripping fastener material is located) a fourth strip 58 of the self-gripping fastener material. With the fourth strip 5S of fastening material at this position, this strip is positioned to bear against, and engage, the third strip 54 of self-gripping fastener material at a time when the holding strap 56 is extended through the buckle 50 and is doubled back upon itself as shown in FIG. 3.

OPERATION

In utilizing the weightlifting belt of the invention, the belt body 10 is first gripped by the user adjacent its opposite ends 28 and 30. The belt is then wrapped around the user's body, with that side of the belt which faces toward the viewer in FIG. 2 of the drawings placed adjacent the body. When the belt has been thus wrapped around the abdominal zone of the body, the strip 3B of self-gripping fastener material will be positioned to be covered by, and contacted with, the second strip 40 of such self-gripping material. This is illustrated in FIG. 6 of the drawings where the two strips carrying the hook and loop portions of fastener material are shown, and are there identified, of course, by reference numerals 38 and 40. With engagement thus effected between the self-gripping strips 3S and 40, the belt is secured around the body of the user. This securement is not alone tenacious enough to prevent muscular forces of large magnitude developed by the straining muscles at the height of the weightlifting exercise from being sufficient, in occasional instances, to cause the bond between the self-gripping strips 38 and 40 to be loosened or released. Therefore, it is desirable to have a second closure subassembly. Moreover, it is preferable to provide a type of second closure subassembly such that the securement of the weightlifting belt around the body of the user will at all times be certain. For the purpose of providing the second closure subassembly, the holding strap 56 has its free end passed through the opening in the buckle 50 and is then doubled back upon itself until the fourth self-gripping material fastener strip 58 is extended back along the belt and the holding strap 56 is tight. When this is the case, the fourth strip 5S of self-gripping material is pressed against the strip 54 so that securement of the belt is greatly enhanced by this second closure subassembly.

If the belt is properly positioned at this time, the lumbar support pad 32 will bear flatly against the user's back, and will fit easily and comfortably into the concavity at the base of the spine, and will afford firm and comfortable support to the back at this location.

Although a preferred embodiment of the invention has been herein described in order to illustrate the principles of the invention to those skilled in the art in a manner adequate to communicate a clear understanding of the principles of the invention and the advantages of the construction proposed, it will be appreciated that various changes and innovations can be made in the illustrated embodiments of the invention without departure from the basic principles which underlie the invention. Changes of this sort are therefore deemed to be circumscribed by the spirit and scope of the invention, except as the same may be necessarily limited by the appended claims or reasonable equivalents thereof.

What is claimed is:

1. A weightlifting belt comprising:
    an elongated belt body having a pair of opposed ends;
    an elongated backup strap secured over its entire length to one side of the belt body and having a pair of opposed ends spaced inwardly along the length of the elongated belt body from the ends of the belt body;
    first fastening means secured to said belt body adjacent one of the ends thereof and to the side of said belt body to which said backup strap is secured;
    second fastening means secured to said belt body adjacent the other of the ends thereof opposite said one end and one the opposite side thereof from said first fastening means in a position to contact and engage said first fastening means when the ends of said belt body are overlapped, and the weightlifting belt encircles the waist of the wearer;
    a buckle secured to said backup strap adjacent one of the ends thereof, and fixed in its position relative to said belt body;
    an elongated holding strap having a first end secured to said belt body and having a second end spaced from said belt body and dimensioned to pass through said buckle when said weightlifting belt is secured in operative position around the waist of the user;
    third fastening means secured to said holding strap adjacent the second end thereof, and adapted to pass with said second end of said holding strap through said buckle; and
    fourth fastening means connected to said belt body at a location spaced along said backup strap from said one of the ends thereof at which said buckle is located.

2. A weightlifting belt as defined in claim 1 and further characterized as including:
    a lumbar support pad carried on said elongated belt substantially midway between the ends thereof and at a location for contact with the lower spine of the wearer of the belt when the belt is worn.

3. weightlifting belt as defined in claim 2 wherein said first fastening means and said second fastening means are each self-engaging material, and including one of either hooks or loops, so that said first fastening means and said second fastening means become engaged with each other upon pressing the two fastening means against each other.

4. A weightlifting belt as defined in claim 3 wherein said elongated belt body comprises:
    a core positioned internally in the body and including:
        an elongated pad of flexible, resilient material; and
        a rigid plate flatly abutting against said pad over substantially its entire length and supporting said pad; and
    a sleeve extending around a major portion of said core and having a body side and an outer side located on the opposite sides of said elongated belt body.

5. A weightlifting belt as defined in claim 9 wherein said backup strap is a heavy duty webbing material.

6. A weightlifting belt as defined in claim 1 wherein said elongated belt body comprises:
    a core positioned internally in the body and including: an elongated pad of flexible, resilient material; and
    a rigid plate flatly abutting against said pad over substantially its entire length and supporting said pad; and
    a sleeve extending around a major portion of said core and having a body side and an outer side located on the opposite sides of said elongated belt body.

7. A weightlifting belt as defined in claim 6 wherein said belt is further characterized as including:

a lumbar support pad carried on said elongated belt substantially midway between the ends thereof and at a location for contact with the lower spine of the wearer of the belt when the belt is worn.

8. A weightlifting belt as defined in claim 1 wherein said first fastening means and said second fastening means are each self-engaging material, and including one of either hooks or loops, so that said first fastening means and said second fastening means become engaged with each other upon pressing the two fastening means against each other.

9. A weightlifting belt as defined in claim 1 wherein said backup strap has a width substantially equivalent to the width of said belt body.

10. A weightlifting belt as defined in claim 1 wherein said backup strap is a heavy duty webbing material.

* * * * *

UNITED STATES PATENT AND TRADEMARK OFFICE
CERTIFICATE OF CORRECTION

PATENT NO. : 4,964,401

DATED : October 23, 1990

INVENTOR(S) : Roger L. Teigen

It is certified that error appears in the above-identified patent and that said Letters Patent is hereby corrected as shown below:

On the title page:

Item [19] "Taigen" should read --Teigen--.
Item [76] Inventor: "Roger L. Taigen" should read --Roger L. Teigen--.

In the Specification:
In Column 3, lin3 26, delete "1B" and insert -18-.
In Column 4, line 26, delete "3B" and insert -38-.
In Column 4, line 67, delete "5S" and insert -58-.
In Column 5, line 13, delete "3B" and insert -38-.
In Column 5, line 20, delete "3S" and insert -38-.
In Column 5, line 38, delete "5S" and insert -58-.

Signed and Sealed this

Seventeenth Day of March, 1992

Attest:

HARRY F. MANBECK, JR.

*Attesting Officer*  *Commissioner of Patents and Trademarks*